United States Patent
Wulff et al.

(10) Patent No.: US 7,196,030 B2
(45) Date of Patent: Mar. 27, 2007

(54) METHOD FOR PRODUCING ALKOXYLATED PRODUCTS AT OPTIMIZED REACTION PRESSURES

(75) Inventors: Christian Wulff, Mannheim (DE); Michael Stösser, Neuhofen (DE); Georg Heinrich Grosch, Bad Dürkheim (DE); Kai-Uwe Baldenius, Ludwigshafen (DE); Edward Bohres, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 136 days.

(21) Appl. No.: 10/528,414

(22) PCT Filed: Apr. 25, 2003

(86) PCT No.: PCT/EP03/04332

§ 371 (c)(1),
(2), (4) Date: Mar. 18, 2005

(87) PCT Pub. No.: WO2004/033404

PCT Pub. Date: Apr. 22, 2004

(65) Prior Publication Data

US 2006/0004232 A1    Jan. 5, 2006

(30) Foreign Application Priority Data

Sep. 18, 2002 (DE) .............................. 102 43 366

(51) Int. Cl.
C08F 4/02 (2006.01)
(52) U.S. Cl. ....................................... 502/104; 568/679
(58) Field of Classification Search ............. 502/104; 568/679
See application file for complete search history.

(56) References Cited

U.S. PATENT DOCUMENTS

| | | | |
|---|---|---|---|
| 2,508,036 A | 5/1950 | Kosmin | |
| 6,204,357 B1 * | 3/2001 | Ooms et al. | 528/409 |
| 6,355,845 B1 * | 3/2002 | Clement et al. | 568/616 |
| 6,362,126 B1 * | 3/2002 | Grosch et al. | 502/154 |
| 6,627,576 B2 * | 9/2003 | Sugiyama et al. | 502/175 |
| 6,762,278 B2 * | 7/2004 | Hinz et al. | 528/405 |

FOREIGN PATENT DOCUMENTS

| | | |
|---|---|---|
| DE | 102 18 752 | 11/2003 |
| DE | 102 18 753 | 11/2003 |
| DE | 102 18 754 | 11/2003 |
| EP | 0 755 716 | 1/1997 |
| EP | 0 862 977 | 9/1998 |
| EP | 0 892 002 | 1/1999 |
| WO | 94/11330 | 5/1994 |
| WO | 94/11331 | 5/1994 |
| WO | 01/04183 | 1/2001 |

OTHER PUBLICATIONS

O'Lenick, Jr., "A Review of Guerbet Chemistry", pp. 1-16, no date available.

* cited by examiner

*Primary Examiner*—J. A Lorengo
*Assistant Examiner*—Veronica Faison-Gee
(74) *Attorney, Agent, or Firm*—Oblon, Spivak, McClelland, Maier & Neustadt, P.C.

(57) ABSTRACT

The present invention relates to a process for the preparation of at least one alkoxylate comprising the bringing into contact of an alkylene oxide mixture at least comprising ethylene oxide with at least one starter compound in the presence of at least one double-metal cyanide compound, where, during the induction phase, the sum of inert gas partial pressure and ethylene oxide partial pressure is 1.5 bar to 6.0 bar, to the alkoxylates obtainable by such a process, and to the use of such alkoxylates as emulsifier, foam regulator or as wetting agent for hard surfaces.

18 Claims, No Drawings

METHOD FOR PRODUCING ALKOXYLATED PRODUCTS AT OPTIMIZED REACTION PRESSURES

The present invention relates to a process for the preparation of at least one alkoxylate comprising the bringing into contact of an alkylene oxide mixture at least comprising ethylene oxide with at least one starter compound in the presence of at least one double-metal cyanide compound where, during the induction phase, the sum of inert gas partial pressure and ethylene oxide partial pressure is 1.5 bar to 6.0 bar, to the alkoxylates obtainable by such a process, and to the use of such alkoxylates as emulsifier, foam regulator or as wetting agent for hard surfaces.

It is known from the literature that double-metal cyanide compounds (DMC compounds) can be used as catalysts for the reaction of starter molecules having active hydrogen and alkylene oxides, for example in a polymerization reaction. The ring-opening polymerizations of alkylene oxides is described, for example, in EP-A 0 892 002, EP-A 1 0 862 977 and in EP-A 0 755 716. In the polymerization of alkylene oxides, DMC compounds have a high activity as catalyst.

Processes for the alkoxylation of aliphatic alcohols and the resulting alkoxylates are known in principle from the prior art. WO 01/04183, for example, describes a process for the ethoxylation of hydroxy-functional starter compounds which is carried out in the presence of a double-metal cyanide compound as catalyst.

Alkoxylates of aliphatic alcohols are used widely as surfactants, emulsifiers or foam suppressors. The wetting and emulsifying properties depend heavily on the nature of the alcohol and the nature and amount of the alkoxide adducts.

WO 94/11330 relates to alkoxylates of 2-propylheptanol and their use. In the alkoxylates, 2-propylheptanol reacted firstly with 1 to 6 mol of propylene oxide and then with 1 to 10 mol of ethylene oxide in the presence of alkali metal hydroxides as catalyst is present. In the examples, 2-propylheptanol reacted firstly with 4 mol of propylene oxide and then 6 mol of ethylene oxide is used. It is stated that the alkylene oxide adducts exhibit an improved relationship of foaming behavior to detergency effect. In addition, it is stated that the alkoxylates exhibit good wetting behavior. They are used in detergent compositions for the cleaning of textile materials. WO 94/11331 relates to the use of such alkoxylates.

U.S. Pat. No. 2,508,036 likewise relates to the use of 2-n-propylheptanol ethoxylates which contain 5 to 15 mol of ethylene oxide as wetting agents in aqueous solutions. It is stated that the products can be used as surfactants in detergents.

DE 102 18 754 and DE 102 18 753 relate to the use of $C_{10}$-alkanol alkoxylate mixtures, in particular alkanol ethoxylate mixtures, such $C_{10}$-alkanol alkoxylate mixtures and processes for their preparation. DE 102 18 752 likewise describes alkoxylate mixtures and detergents comprising these and also processes for the preparation of the alkoxylate mixtures and the use of the detergent for the washing or cleaning of textiles.

During the alkoxylation, in particular the ethoxylation, of starter compounds in the presence of double-metal cyanide compounds, two problems in particular arise. Firstly, the induction phase of the reaction is sometimes very long, which leads to an extension of the reaction times and to increased costs, and secondly the activity of the catalyst during the reaction often slowly decreases until the reaction rate is no longer adequate.

It is an object of the invention to provide a process for the ethoxylation of starter compounds with improved conversion of the starter compound, shortened induction phase and improved catalyst stability.

We have found that this object is achieved according to the invention by a process for the preparation of at least one alkoxylate comprising the bringing into contact of an alkylene oxide mixture at least comprising ethylene oxide with at least one starter compound in the presence of at least one double-metal cyanide compound of the formula I:

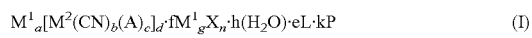

$$M^1_a[M^2(CN)_b(A)_c]_d \cdot fM^1_g X_n \cdot h(H_2O) \cdot eL \cdot kP \quad (I)$$

in which $M^1$ is at least one metal ion chosen from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$, $Ru^{3+}$, $M^2$ is at least one metal ion chosen from the group consisting of $Fe^{2+}$, $Fe^{3+}$, $Co^{2+}$, $C^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, $Ir^{3+}$, A and X, independently of one another, are an anion chosen from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate or hydrogencarbonate, L is a water-miscible ligand chosen from the group consisting of alcohols, aldehydes, ketones, ethers, polyethers, esters, polyesters, polycarbonate, ureas, amides, primary, secondary and tertiary amines, ligands with pyridine nitrogen, nitriles, sulfides, phosphides, phosphites, phosphines, phosphonates and phosphates, k is a fraction or integer greater than or equal to zero, and P is an organic additive, a, b, c, d, g and n are chosen such that the electroneutrality of the compound (I) is ensured, where c may be 0, e is the number of ligand molecules, a fraction or integer greater than 0, or 0, f and h, independently of one another, are a fraction or integer greater than 0, or 0, wherein, during the induction phase, the sum of inert gas partial pressure and ethylene oxide partial pressure is 1.5 bar to 6.0 bar.

Induction phase is understood as meaning that the alkoxylation reaction does not start immediately after the bringing into contact of the alkylene oxide with the starter alcohol and the double-metal cyanide compound, but is delayed by a certain time. This induction phase is evident, for example, from the fact that, after a small amount of alkylene oxide has been metered in, a certain pressure results in the reactor which remains constant for a certain time and rapidly decreases at the end of the induction phase. Following the pressure drop, the reaction has started, and the further metered addition of the alkylene oxide can take place.

According to the invention, the sum of inert gas partial pressure and ethylene oxide partial pressure during the induction phase is 1.5 to 6.0 bar, preferably 1.5 to 5.0 bar, particularly preferably 1.5 to 3.0 bar. This pressure range is particularly advantageous since on the one hand a rapid start-up of the reaction is observed, but on the other hand the pressure is not too high. The total pressure is made up of the partial pressures of the individual gases. If only inert gas and ethylene oxide are used, the sum of inert gas partial pressure and ethylene oxide partial pressure corresponds to the total pressure. A high total pressure at the start of the reaction would, for example, require expensive reaction vessels and thus make the overall process more expensive.

In a preferred embodiment, in the process according to the invention, firstly the reactor is charged with an inert gas and then the alkylene oxide mixture comprising at least ethylene oxide is added. The inert gas partial pressure is, according to the invention, for example 1.5 to 6.0 bar, preferably 1.5 bar to 3.0 bar, preferably 1.5 to 2.5 bar, particularly preferably 1.5 to 2.0 bar.

For the purposes of the present invention, the ethylene oxide partial pressure is less than or equal to the inert gas partial pressure, where the sum of inert gas partial pressure and ethylene oxide partial pressure is 1.5 bar to 6.0 bar.

This procedure has the advantage that using the inert gas a partial pressure can be established and then the alkylene oxide mixture at least comprising ethylene oxide can be metered in, where the ethylene oxide concentration in the gas phase is not too high. For safety reasons, a concentration of >40%, preferably >50%, of ethylene oxide in the gas phase should be avoided in the reactor since high concentrations may result in spontaneous EO decomposition and thus to overheating or explosion of the reactor.

The ethylene oxide partial pressure is determined in the case of such a procedure essentially through the ratio of the metered addition of ethylene oxide and of the reaction rate of the ethylene oxide. For the purposes of the present invention, the ethylene oxide partial pressure during the induction phase is preferably less than 3.0 bar, in particular less than 1.5 bar, for example less than 1.0 bar.

In the process according to the invention, the reaction vessel can, for example, firstly be filled with a suspension of alcohol and DMC catalyst. The catalyst can then be activated by separating off water, e.g. by heating and/or evacuating the reaction vessel.

The reaction mixture is then advantageously heated to reaction temperature and a nitrogen prepressure is established. In the further course of the process, a starting amount of ethylene oxide, for example, is metered in. After the reaction has started, further ethylene oxide is metered in, the reaction mixture is stirred until all of the ethylene oxide has reacted. The reaction mixture can optionally be worked up further.

In a preferred embodiment, the present invention therefore provides a process where, during the induction phase, the inert gas partial pressure is 1.5 bar to 6.0 bar, preferably 1.5 to 3.0 bar. For the purposes of the present invention, suitable inert gases are, for example, nitrogen, $CO_2$ or noble gases such as argon or mixtures thereof, preferably nitrogen.

According to the invention, the pressure changes during the reaction. Following a possible initial pressure drop as the reaction starts, the pressure increases over the course of the reaction since the fill level in the reactor increases and the gas mixture is compressed. According to the invention, it is preferred that the total pressure, in particular the sum of inert gas partial pressure and ethylene oxide partial pressure, in the course of the reaction does not exceed 20 bar, for example does not exceed 11 bar, preferably does not exceed 6 bar, in particular does not exceed 3.5 bar.

In a preferred embodiment, the present invention therefore provides a process where the total pressure does not exceed 11 bar in the course of the reaction.

The process according to the invention is carried out at temperatures of from 80 to 190° C.

The process according to the invention for the preparation of an alkoxylate is carried out in the presence of a double-metal cyanide compound of the formula I as catalyst:

$$M^1_a[M^2(CN)_b(A)_c]_d \cdot fM^1_g X_n \cdot h(H_2O) \cdot eL \cdot kP \qquad (I)$$

in which $M^1$ is at least one metal ion chosen from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$, $Ru^{3+}$, $M^2$ is at least one metal ion chosen from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, $Ir^{3+}$, A and X, independently of one another, are an anion chosen from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate or hydrogencarbonate, L is a water-miscible ligand chosen from the group consisting of alcohols, aldehydes, ketones, ethers, polyethers, esters, polyesters, polycarbonate, ureas, amides, primary, secondary and tertiary amines, ligands with pyridine nitrogen, nitriles, sulfides, phosphides, phosphites, phosphines, phosphonates and phosphates, k is a fraction or integer greater than or equal to zero, and P is an organic additive, a, b, c, d, g and n are chosen such that the electroneutrality of the compound (I) is ensured, where c may be 0, e is the number of ligand molecules, a fraction or integer greater than 0, or 0, f and h, independently of one another, are a fraction or integer greater than 0, or 0.

Organic additives P which can be mentioned are: polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylamide-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkyleneimines, maleic acid and maleic anhydride copolymers, hydroxyethylcellulose, polyacetates, ionic surface-active and interface-active compounds, bile acid or salts thereof, esters or amides, carboxylic esters of polyhydric alcohols and glycosides.

These catalysts may be crystalline or amorphous. When k is zero, crystalline double-metal cyanide compounds are preferred. When k is greater than zero, either crystalline, partially crystalline or else substantially amorphous catalysts are preferred.

There are various preferred embodiments of the modified catalysts. One preferred embodiment covers catalysts of the formula (I) in which k is greater than zero. The preferred catalyst then comprises at least one double-metal cyanide compound, at least one organic ligand and at least one organic additive P.

In another preferred embodiment, k is zero, e is optionally also zero and X is exclusively a carboxylate, preferably formate, acetate and propionate. Such catalysts are described in WO 99/16775. In this embodiment, preference is given to crystalline double-metal cyanide catalysts. Also preferred are double-metal cyanide catalysts as described in WO 00/74845, which are crystalline and platelet-like.

In a preferred embodiment, the present invention therefore provides a process in which the double-metal cyanide compound used as catalyst is crystalline.

The modified catalysts are prepared by combining a metal salt solution with a cyanometallate solution, which may optionally contain both an organic ligand L and also an organic additive P. Subsequently, the organic ligand and optionally the organic additive are added. In a preferred embodiment of the catalyst preparation, an inactive double-metal cyanide phase is firstly prepared, and this is then converted into an active double-metal cyanide phase by recrystallization, as described in PCT/EP01/01893.

In another preferred embodiment of the catalysts, f, e and k do not equal zero. These are double-metal cyanide catalysts which contain a water-miscible organic ligand (generally in amounts of from 0.5 to 30% by weight) and an organic additive (generally in amounts of from 5 to 80% by weight), as described in WO 98/06312. The catalysts can either be prepared with vigorous stirring (24 000 rpm using Turrax) or with stirring, as described in U.S. Pat. No. 5,158,922.

Particularly suitable catalysts for the alkoxylation are double-metal cyanide compounds which contain zinc, cobalt or iron or two thereof. Prussian blue, for example, is particularly suitable.

Preference is given to using crystalline DMC compounds. In a preferred embodiment, a crystalline DMC compound of the Zn—Co type which comprises zinc acetate as further metal salt component is used as catalyst. Such compounds crystallize in monoclinic structure and have a platelet-like habit. Such compounds are described, for example, in WO 00/74845 or PCT/EP01/01893.

DMC compounds suitable as catalysts may, in principle, be prepared by all ways known to the person skilled in the art. For example, the DMC compounds can be prepared by direct precipitation, incipient wetness method, by preparing a precursor phase and subsequent recrystallization.

The DMC compounds can be used as powder, paste or suspension, or be molded to give a shaped body, be converted to moldings, foams or the like, or be applied to moldings, foams or the like.

The catalyst concentration used for the alkoxylation, based on the final quantity structure, is typically less than 2000 ppm (i.e. mg of catalyst per kg of product), preferably less than 1000 ppm, in particular less than 500 ppm, particularly preferably less than 100 ppm, for example less than 50 ppm or 35 ppm, especially preferably less than 25 ppm.

In a preferred embodiment, the present invention provides a process in which the double-metal cyanide compound is used in an amount of 100 ppm or less, based on the final quantity structure.

In further embodiments, the present invention provides a process where at least one of the following properties is satisfied:

(1) $M^1$ is chosen from the group $Zn^{2+}$, $Fe^{2+}$, $Fe^{3+}$, $Co^{3+}$, $Ni^{2+}$, $Mn^{2+}$, $Co^{2+}$;

(2) $M^2$ is chosen from the group $Fe^{2+}$, $Fe^{3+}$, $Co^{3+}$, or particularly preferably a process where $M^1$ is $Zn^{2+}$ and $M^2$ is $Co^{3+}$.

Suitable starter compounds are all compounds which have an active hydrogen. According to the invention, preferred starting compounds are OH-functional compounds.

Especially preferred starter compounds are monofunctional or polyfunctional alcohols having 2 to 24 carbon atoms, especially monofunctional linear or once or more branched alkanols with 2 to 24 carbon atoms.

Suitable branched alcohols are for example alcohols with a hydroxyl group in the 2-, 3-, 4-position etc. The alkyl group may be linear or once again branched and carry for example methyl or ethyl substituents. Examples of suitable alcohols are 2-decanol, 2-dodecanol, 2-tetradecanol, 2-hexadecanol, each alcohol being obtainable by adding water to an α-olefine, (6-ethyl)-3-nonanol, obtainable by reaction of 2-ethylhexanol with acetone and subsequent hydrogenation of 2-hexadecanol respectively 2-octa-decanol, obtainable by reaction of a $C_{13}/C_{15}$-aldehyd with acetone, 3-nonadecanol respectively (3-methyl)-2-octadecanol, (3-metyhl)-2-hexadecanol, 3-heptadecanol, obtainable by reaction of a $C_{13}/C_{15}$-aldehyd with 2-butanone. The reaction products are based $C_{13}/C_{15}$-aldehyd are in a technical mixture branched in α-position for approximately 40 to 50%.

Examples of further suitable alcohols are linear $C_{12}$-$C_{14}$-alkanes with a hydroxyl group in an none-terminal position of the chain or mixtures thereof (for example Saftanol®-alcohols of Nippon Shokubai or Tergitol®-alcohols of Dow).

Starter compounds which can be used in the process according to the invention are, in particular, monofunctional alcohols having 6 to 18 carbon atoms, preferably alcohols having 8 to 15 carbon atoms, such as, for example, tridecanol or propylheptanol.

Alcohols suitable according to the invention are thus, in particular, octanol, 2-ethylhexanol, nonanol, decanol, undecanol, dodecanol, 2-butyloctanol, tridecanol, tetradecanol, pentadecanol, isooctanol, isononanol, isodecanol, isoundecanol, isododecanol, isotridecanol, isotetradecanol, isopentadecanol, preferably isodecanol, 2-propylheptanol, tridecanol, isotridecanol or mixtures of C13- to C15-alcohols or mixtures of 2-propylheptanol with structurally isomeric $C_{10}$-alcohols.

The present invention therefore also provides, in a preferred embodiment, a process in which the starter compound is a monofunctional linear or branched alcohol having 2 to 24, preferably 8 to 15 carbon atoms.

For example, the alcohols used according to the invention as starter compound are Guerbet alcohols, in particular ethylhexanol, propylheptanol, butyloctanol. The present invention therefore also provides, in a particularly preferred embodiment, a process where the starter compound is a Guerbet alcohol.

The alcohols used as starter compound may, according to the invention, also be mixtures of different isomers. For example, propylheptanol can be obtained starting from valeraldehyde by aldol condensation and subsequent hydrogenation. The preparation of valeraldehyde and the corresponding isomers takes place by hydroformylation of butene, as described, for example, in U.S. Pat. No. 4,287,370; Beilstein E IV 1, 32 68, Ullmanns Encyclopedia of Industrial Chemistry, 5th edition, Volume A1, pages 323 and 328. The subsequent aldol condensation is described, for example, in U.S. Pat. No. 5,434,313 and Römpp, Chemie Lexikon, 9th edition, keyword "Aldol addition" page 91. The hydrogenation of the aldol condensation product follows general hydrogenation conditions.

Furthermore, 2-propylheptanol can be prepared by condensation of 1-pentanol (as a mixture of the corresponding methyl-1-butanols) in the presence of KOH at elevated temperatures, see e.g. Marcel Guerbet, C. R. Acad Sci Paris 128, 511, 1002 (1899). Furthermore, reference is made to Rbmpp, Chemie Lexikon, 9th edition, Georg Thieme Verlag Stuttgart, and the citations given therein, and also Tetrahedron, Vol. 23, pages 1723 to 1733.

In addition, secondary alcohols or mixtures are also suitable. These may be obtainable, for example, by the addition of ketones onto aldehydes with subsequent hydrogenation, as described in DE 100 35 617.6. Preference is given here to methyl ketones, such as acetone, methyl ethyl ketone or methyl isobutyl ketone. Also suitable are paraffin oxidation products which are formed, for example, by Bashkirov oxidation. Here, products of $C_{11}$-$C_{16}$-paraffin mixtures, particularly products of $C_{12}$-$C_{14}$-paraffin mixtures, are preferred. Suitable alcohols are also, for example, secondary alcohols, which are obtained by addition of water onto olefins or by free-radical or other oxidation of olefins.

The alkylene oxide mixture used in the process according to the invention can, as well as ethylene oxide, comprise further alkylene oxides, in particular a further alkylene oxide chosen from the group consisting of propylene oxide, butylene oxide and pentylene oxide.

In this case, for the purposes of the present invention, the alkylene oxide mixtures preferably have an ethylene oxide fraction of more than 50% (% by mass), in particular of more than 75%, particularly preferably of more than 95%, for example of more than 99%.

In a preferred embodiment, according to the invention, no further alkylene oxide is used alongside ethylene oxide.

The present invention therefore provides, in a further embodiment, a process where the alkylene oxide mixture comprises ethylene oxide and a further alkylene oxide chosen from the group consisting of propylene oxide, butylene oxide and pentylene oxide.

In a further embodiment, the present invention thus also provides a process in which no further alkylene oxide is used alongside ethylene oxide.

Preferably, the alkylene oxide mixture is used in the process according to the invention in amounts such that the resulting degree of alkoxylation is, for example, in the range from 2 to 20, preferably in the range from 3 to 14.

Moreover, the present invention also provides alkoxylates obtainable by the above-described process.

The alkoxylates according to the invention exhibit good wetting on hard surfaces. The advantageous wetting behavior of the mixtures according to the invention can be determined, for example, by measurements of the contact angle on glass, polyethylene oxide or steel. The alkoxylates according to the invention further exhibit good emulsifying behavior combined with easy biodegradability.

The present invention thus also provides for the use of an alkoxylate according to the invention, in particular an ethoxylate, or an alkoxylate prepared by a process according to the invention, in particular an ethoxylate, as emulsifier, foam regulator or as wetting agent for hard surfaces, in particular for use in detergents, surfactant formulations for the cleaning of hard surfaces, humectants, cosmetic, pharmaceutical and crop protection formulations, paints, coating compositions, adhesives, leather-degreasing compositions, formulations for the textile industry, fiber processing, metal processing, food industry, water treatment, paper industry, fermentation or mineral processing and in emulsion polymerizations.

In addition, the alkoxylates prepared according to the invention serve to reduce the interfacial tension, for example in aqueous surfactant formulations. The reduced interfacial tension can, for example, be determined by the pendant-drop method. This also results in a better effect of the alkoxylates according to the invention as emulsifier or coemulsifier. The alkoxylates according to the invention can also be used for reducing the interfacial tension in short times of customarily less than one second, or for accelerating the establishment of the interfacial tension in aqueous surfactant formulations.

Preferred fields of use for the alkoxylates according to the invention are described in more detail below.

The alkoxylates according to the invention are preferably used in the following fields:

Surfactant formulations for the cleaning of hard surfaces: suitable surfactant formulations which can be additized with the alkoxylates according to the invention are described, for example, in Formulating Detergents and Personal Care Products by Louis Ho Tan Tai, AOCS Press, 2000.

They comprise, for example, as further components, soap, anionic surfactants, such as LAS or paraffinsulfonates or FAS or FAES, acid such as phosphoric acid, amidosulfonic acid, citric acid, lactic acid, acetic acid, other organic and inorganic acids, solvents, such as ethylene glycol, isopropanol, complexing agents, such as EDTA, NTA, MGDA, phosphonates, polymers, such as polyacrylates, copolymers of maleic acid-acrylic acid, alkali donors, such as hydroxides, silicates, carbonates, perfume oils, oxidizing agents, such as perborates, peracids or trichloroisocyanuric acid, Na or K dichloroisocyanurates, enzymes; see also Milton J. Rosen, Manilal Dahanayake, Industrial Utilization of Surfactants, AOCS Press, 2000 and Nikolaus Schönfeldt, Grenzflächenaktive Ethylenoxidaddukte [Interface-active ethylene oxide adducts]. This also covers, in principle, formulations for the other applications mentioned. They may be household cleaners, such as all-purpose cleaners, dishwashing detergents for manual and automatic dishwashing, metal degreasing, industrial applications, such as cleaners for the food industry bottlewashing etc. They may also be printing roll and printing plate cleaners in the printing industry. Suitable further ingredients are known to the person skilled in the art.

Humectants, in particular for the printing industry.

Cosmetic, pharmaceutical and crop protection formulations. Suitable crop protection formulations are described, for example, in EP-A-0 050 228. Further ingredients customary for crop protection compositions may be present.

Paints and coating compositions, dyes, pigment preparations and adhesives in the coatings and polymer film industry.

Leather-degreasing compositions.

Formulations for the textile industry, such as leveling agents or formulations for yarn cleaning.

Fiber processing and auxiliaries for the paper and pulp industry.

Metal processing, such as metal finishing and electroplating sector.

Food industry.

Water treatment and production of drinking water.

Fermentation.

Mineral processing and dust control.

Building auxiliaries.

Emulsion polymerization and preparation of dispersions.

Coolants and lubricants.

Such formulations usually comprise ingredients such as surfactants, builders, fragrances and dyes, complexing agents, polymers and other ingredients. Typical formulations are described, for example, in WO 01/32820. Further ingredients suitable for various applications are described, for example, in EP-A-0 620 270, WO 95/27034, EP-A-0 681 865, EP-A-0 616 026, EP-A-0 616 028, DE-A-42 37 178 and U.S. Pat. No. 5,340,495 and in Schönfeldt, see above.

Generally, the alkoxylates according to the invention can be used in all fields in which the action of interface-active substances is necessary.

The present invention therefore also provides detergents, cleaners, wetting agents, coating compositions, adhesive compositions, leather-degreasing compositions, humectants or textile-treatment compositions or cosmetic, pharmaceutical or crop protection formulation comprising an alkoxylate according to the invention or an alkoxylate prepared by a process according to the invention. The products here preferably comprise 0.1 to 20% by weight of the alkoxylates.

The present invention will be illustrated in more detail below by reference to examples.

EXAMPLES

Preparation Example

Double-metal Cyanide Catalyst 16000 g of aqueous hexacyanocobaltic acid (cobalt content: 9 g/l) were initially introduced into a stirred vessel with a volume of 30 l and equipped with a propeller stirrer, immersion tube for the metered addition, pH probe and scattered light probe, and heated to 50° C. with stirring. Then, with stirring at a stirrer output of 0.4 W/l, 9224 g of aqueous zinc acetate dihydrate solution (zinc content: 2.6% by weight), which had likewise been heated to 50° C., were introduced over the course of 15 minutes.

351 g of Pluronic® PE 6200 (BASF AG) were added to this precipitate suspension, and the mixture was stirred for a further 10 minutes.

Then, a further 3690 g of aqueous zinc acetate dihydrate solution (zinc content: 2.6% by weight) were metered in over the course of 5 minutes with stirring with a stirring energy of 1 W1.

The suspension was after-stirred for two hours. During this period, the pH dropped from 4.02 to 3.27 and then remained constant. The precipitate suspension obtained in this way was then filtered off and washed on the filter with 6 times the cake volume of water.

The moist filtercake was dried and dispersed in Tridekanol® N by means of a gap rotor mill. The suspension obtained had a multimetal cyanide content of 5% by weight.

Example 1

Comparative Example, 2-propylheptanol+8 EO at a Maximum Total Pressure of 1.70 Bar 316 g (2.0 mol) of 2-propyl-1-heptanol (isomer mixture of 87% 2-propyl-1-heptanol, 11% of 2-propyl-4-methyl-1-hexanol, <1% 2-propyl-5-methyl-1-hexanol) and 35 ppm of double-metal cyanide catalyst (based on the product) were dewatered at a temperature of 100° C. and about 20 mbar for two hours in a 3.5 l pressure autoclave. The system was then flushed with nitrogen three times and a temperature of 140° C. was set. After the temperature had been reached, a total of 704 g (16.0 mol) of ethylene oxide were to be metered in, with stirring, at a maximum total pressure of 1.70 bar (absolute). Following the addition of 582 g of ethylene oxide, a reaction could no longer be detected (virtually no pressure decrease, virtually no evolution of heat).

Example 2

Starting the Reaction With Pressure Increase

The reaction mixture from Example 1 was stirred further and the total pressure increased to 6.0 bar by adding ethylene oxide. An adequate pressure decrease and temperature increase could again be detected, meaning that the remaining amount of ethylene oxide could be reacted successfully.

When the metered addition of ethylene oxide was complete, the mixture was stirred for a further 1 h at 140° C., then cooled to 80° C., and the reactor was flushed three times with nitrogen, then evacuated to 20 mbar to degas, and emptied. The reaction product was not filtered and corresponded to the desired product.

Example 3

Comparative Example, 2-propylheptanol+1.2 PO+6 EO at a Maximum EO Pressure of 1.70 Bar 316 g (2.0 mol) of 2-propyl-1-heptanol and 35 ppm of double-metal cyanide catalyst (based on the product) were dewatered at a temperature of 100° C. and about 20 mbar for two hours in a pressure autoclave. The system was subsequently flushed three times with nitrogen and then heated to 140° C. After the temperature had been reached, a total of 140 g (2.4 mol) of propylene oxide were metered in, with stirring, at 140° C. When the PO metered addition was complete, the mixture was stirred for a further 15 minutes at 140° C.

The temperature is held at 140° C., and then 528 g (12.0 mol) of ethylene oxide were metered in at a maximum total pressure of 1.70 bar. Following the addition of 424 g of ethylene oxide, an adequate reaction could no longer be detected (virtually no pressure decrease, virtually no evolution of heat).

Example 4

Starting the Reaction with Pressure Increase

The reaction mixture from example 3 was further stirred and the total pressure increased to 6.0 bar by adding ethylene oxide. An adequate pressure decrease and temperature increase could again be detected, meaning that the remaining amount of ethylene oxide could be reacted successfully.

When the metered addition of ethylene oxide was complete, the mixture was stirred for a further 1 h at 140° C., then cooled to 80° C., and the reactor was flushed three times with nitrogen, then evacuated to 20 mbar to degas, and emptied. The reaction product was not filtered and corresponded to the desired product.

Example 5

2-propylheptanol+8 EO at a Maximum EO Pressure of 2.5 Bar 316 g (2.0 mol) of 2-propyl-1-heptanol and 35 ppm of double-metal cyanide catalyst (based on the product) were dewatered at a temperature of 100° C. and about 20 mbar for two hours in a pressure autoclave. The system was then flushed three times with nitrogen and then a total pressure of 2.5 bar of nitrogen (absolute) at 140° C. was established. After the temperature had been reached, a total of 704 g (16.0 mol) of ethylene oxide were metered in, with stirring, at a maximum total pressure of 5.0 bar (absolute). When the metered addition of ethylene oxide was complete, the mixture was stirred for a further 1 h at 140° C., then cooled to 80° C., and the reactor was flushed three times with nitrogen, then evacuated to 20 mbar to degas, and emptied. The reaction product was not filtered and corresponded to the desired product.

Example 6

2-propylheptanol+1.2 PO+6 EO at a Maximum EO Pressure of 2.5 Bar 316 g (2.0 mol) of 2-propyl-1-heptanol (isomer mixture of 87% 2-propyl-1-heptanol, 11% 2-propyl-4-methyl-1-hexanol, <1% 2-propyl-5-methyl-1-hexanol) and 35 ppm of double-metal cyanide catalyst (based on the product) were dewatered at a temperature of 100° C. and about 20 mbar for two hours in a pressure autoclave. The system was subsequently flushed three times with nitrogen and then heated to 140° C. After the temperature had been reached, a total of 140 g (2.4 mol) of propylene oxide were metered in, with stirring, at 140° C. When the PO metered addition was complete, the mixture was stirred for a further 15 minutes at 140° C.

A total pressure of 2.5 bar of nitrogen (absolute) at 140° C. was then established and afterwards the metered addition of a total of 528 g (12.0 mol) of ethylene oxide at a maximum total pressure of 5.0 bar (absolute, 140° C.) was started. When the metered addition of ethylene oxide was complete, the mixture was stirred for a further 1 h at 140° C., then cooled to 80° C., and the reactor was flushed three times with nitrogen, then evacuated to 20 mbar to degas, and emptied. The reaction product was not filtered and corresponded to the desired product.

We claim:

1. A process for the preparation of at least one alkoxylate comprising:

bringing into contact an alkylene oxide mixture comprising ethylene oxide with at least one starter compound in the presence of at least one double-metal cyanide compound of the formula 1:

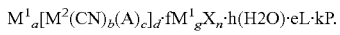

$M^1_a[M^2(CN)_b(A)_c]_d \cdot fM^1_g X_n \cdot h(H_2O) \cdot eL \cdot kP$.

wherein $M^1$ is a metal ion selected from the group consisting of $Zn^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^+$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$, and $Ru^{3+}$;

$M^2$ is a metal ion selected from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, and $Ir^{3+}$;

A and X, independently of one another, are anions, each of which is selected from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate or and hydrogencarbonate;

L is a water-miscible ligand selected from the group consisting of alcohols, aldehydes, ketones, ethers, polyethers, esters, polyesters, polycarbonate, ureas, amides, primary, secondary and tertiary amines, ligands with pyridine nitrogen, nitriles, sulfides, phosphides, phosphates, phosphines, phosphonates and phosphates;

k is a fraction or an integer, wherein the value of k is greater than or equal to zero;

P is at least one organic additive selected from the group consisting of polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylamide-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkyleneimines, maleic acid and maleic anhydride copolymers, hydroxyethylcellulose, polyacetates, ionic surface-active and interface-active compounds, bile acid or salts thereof, esters or amides, carboxylic esters of polyhydric alcohols, and glycosides;

a, b, c, d, g and n are chosen such that the electroneutrality of the compound I is ensured;

e is the number of ligand molecules, wherein e is a fraction or an integer, and wherein the value of e is greater than or equal to 0; and each of f and h, independently of one another, is a fraction or an integer wherein each off and h, independently of each other, has a value greater than or equal to 0;

wherein, during the induction phase, the sum of the inert gas partial pressure and the ethylene oxide partial pressure is 1.5 bar to 6.0 bar; and wherein the starter compound is a Guerbet alcohol.

2. The process of claim 1, wherein the total pressure does not exceed 11 bar over the course of the reaction.

3. The process of claim 1, wherein:
(1) $M^1$ is selected from the group consisting of $Zn^{2+}$, $Fe^{2+}$, $Fe^{3+}$, $Co^{3+}$, $Ni^{2+}$, $Mn^{2+}$ and $Co^{2+}$; or
(2) $M^2$ is selected from the group consisting of $Fe^{e+}$, $Fe^{3+}$, and $Co^{3+}$.

4. The process of claim 1, wherein $M^1$ is $Zn^{2+}$ and $M^2$ is $Co^{3+}$.

5. The process of claim 1, wherein the double-metal cyanide compound catalyst is crystalline.

6. A process for the preparation of at least one alkoxylate comprising:

bringing into contact an alkylene oxide mixture comprising ethylene oxide with at least one starter compound in the presence of at least one double-metal cyanide compound of the formula 1:

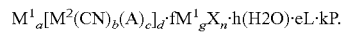

$M^1_a[M^2(CN)_b(A)_c]_d \cdot fM^1_g X_n \cdot h(H_2O) \cdot eL \cdot kP$.

wherein $M^1$ is a metal ion selected from the group consisting of $Zn^{2+}$, $F^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $H^{2+}$, $Pd^{2+}$, $Pt^{2+,}$ $V^{2+}$, $Mg^+$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$, and $Ru^{3+}$;

$M^2$ is a metal ion selected from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, and $Ir^{3+}$;

A and X, independently of one another, are anions, each of which is selected from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate or and hydrogencarbonate;

L is a water-miscible lagand selected from the group consisting of alcohols, aldehydes, ketones, ethers, polyethers, esters, polyesters, polycarbonate, ureas, amides, primary, secondary and tertiary amines, ligands with pyridine nitrogen, nitriles, sulfides, phosphides, phosphates, phosphines, phosphonates and phosphates;

k is a fraction or an integer, wherein the value of k is greater than or equal to zero;

P is an organic additive, a, b, c, d, g and n are chosen such that the electroneutrality of the compound I is ensured;

e is the number of ligand molecules, wherein e is a fraction or an integer, and wherein the value of e is greater than or equal to 0; and each of f and h, independently of one another, is a fraction or an integer wherein each of f and h, independently of each other, has a value greater than or equal to 0;

wherein, during the induction phase, the sum of the inert gas partial pressure and the ethylene oxide partial pressure is 1.5 bar to 6.0 bar, and wherein the starter compound is a Guerbet alcohol, wherein the alkylene oxide mixture has an ethylene oxide fraction of more than 99%.

7. An alkoxylate obtained by the process of claim 1.

8. The process of claim 1, wherein c has a value of 0.

9. The process of claim 1, wherein
   (1) $M^1$ is selected from the group consisting of $Zn^{2+}$, $Fe^{3+}$, $Fe^+$, $Co^{3+}$, $Ni^{2+}$, $Mn^{2+}$ and $Co^{2+}$; and
   (2) $M^2$ is selected from the group consisting of $Fe^{2+}$, $Fe^{3+}$, and $Co^{3+}$.

10. The process of claim 1, wherein the alkylene oxide mixture has an ethylene oxide fraction of more than 99%.

11. The process of claim 1, wherein e is greater than zero.

12. The process of claim 1, wherein f is greater than zero.

13. The process of claim 1, wherein g is greater than zero.

14. The process of claim 1, wherein k is greater than zero.

15. The process of claim 1, wherein e is zero.

16. The process of claim 1, wherein f is zero.

17. The process of claim 1, wherein g is zero.

18. The process of claim 1, wherein k is zero.

* * * * *